United States Patent
Kumazawa (10) Patent No.: US 9,522,074 B2
(45) Date of Patent: Dec. 20, 2016

(54) STENT DELIVERY SYSTEM

(71) Applicant: TERUMO KABUSHIKI KAISHA, Shibuya-ku (JP)

(72) Inventor: Takashi Kumazawa, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 149 days.

(21) Appl. No.: 14/032,917

(22) Filed: Sep. 20, 2013

(65) Prior Publication Data

US 2014/0088682 A1    Mar. 27, 2014

(30) Foreign Application Priority Data

Sep. 21, 2012 (JP) ................. 2012-208891

(51) Int. Cl.
| | | |
|---|---|---|
| *A61F 2/958* | (2013.01) | |
| *A61F 2/915* | (2013.01) | |
| *A61M 25/10* | (2013.01) | |

(52) U.S. Cl.
CPC ...... *A61F 2/958* (2013.01); *A61F 2002/91558* (2013.01); *A61M 2025/1004* (2013.01)

(58) Field of Classification Search
CPC .. A61F 2/958; A61F 2002/91558; A61F 2/95; A61F 2002/9505; A61F 2002/9511; A61F 2002/9522; A61F 2002/9583; A61F 2002/9586; A61F 2/97; A61F 2/00; A61F 2/04; A61F 2/07; A61F 2/82; A61F 2/2433; A61M 2025/1004; A61M 25/1002; A61M 25/1006; A61M 25/1009; A61M 25/10; A61B 17/22032; Y10S 264/06

(Continued)

(56) References Cited

U.S. PATENT DOCUMENTS 6,293,959 B1    9/2001  Miller et al.
6,863,683 B2 *  3/2005  Schwager et al. ........... 623/1.11
(Continued)

FOREIGN PATENT DOCUMENTS

EP    1295570 A2      3/2003
JP    2008-086463 A   4/2008
(Continued)

OTHER PUBLICATIONS

Extended European Search Report issued on Jan. 29, 2014 by European Patent Office in corresponding European Patent Application No. 13184958.0 (6 pgs).

(Continued)

*Primary Examiner* — Eric Rosen
*Assistant Examiner* — George J Ulsh
(74) *Attorney, Agent, or Firm* — Buchanan Ingersoll & Rooney PC (57) ABSTRACT

A stent delivery system is configured so that its outer diameter can be reduced when the balloon is folded and the stent is mounted on the folded balloon. The stent delivery system includes a balloon which is expandable by injection of fluid inside the balloon, and is folded in the form of stacked layers around an outer circumference of an elongated inner tube. The stent delivery system also includes a stent having a plurality of annular parts, each formed with a wire in an annular shape and arranged in the direction of the axis of the stent, and a plurality of connecting parts connecting the neighboring annular parts. All the connecting parts are arranged on the outer circumference of the balloon in a manner that each of the connecting parts is positioned on a minimum-layered portion having the smallest number of stacked layers.

18 Claims, 7 Drawing Sheets

(58) Field of Classification Search
USPC .................................................. 623/1.11–1.15
See application file for complete search history.

(56) References Cited

U.S. PATENT DOCUMENTS

| | | |
|---|---|---|
| 2009/0187239 A1 | 7/2009 | Goto |
| 2010/0063571 A1 | 3/2010 | Roach et al. |
| 2011/0152997 A1* | 6/2011 | Kelly et al. .................. 623/1.12 |

FOREIGN PATENT DOCUMENTS

| | | |
|---|---|---|
| JP | 2012070875 A | 4/2012 |
| WO | 2008/038830 A1 | 3/2008 |
| WO | 2009/147653 A1 | 12/2009 |

OTHER PUBLICATIONS

Official Action (Notice of Reasons for Rejection) issued Feb. 1, 2016 by the Japanese Patent Office in counterpart Japanese Application No. 2012-208891, including an English translation (5 pages).

* cited by examiner

STENT DELIVERY SYSTEM

CROSS REFERENCE TO RELATED APPLICATONS

This application claims priority to Japanese Application No. 2012-208891 filed on Sep. 21, 2012, the entire content of which is incorporated herein by reference.

TECHNICAL FIELD

The present invention generally relates to a stent delivery system used for curing a stenosed portion occurred in a living lumen such as a blood vessel.

BACKGROUND DISCUSSION

In recent years, in the field of treating or curing an acute myocardiac infarction or a heart stroke, a method has been employed in which a stent is indwelled in a lesion in a coronary artery (stenosed portion). A similar method may be used to treat or cure a stenosed portion formed in other living lumens, such as other blood vessels, a bile duct, a trachea, an esophagus, a urethra, etc. A stent delivery system used to indwell a stent typically includes a long shaft portion and a balloon which is expandable in a radial direction provided in a distal end side of the shaft portion. A cylindrical stent formed of a metal wire is positioned (mounted) on the outer circumference of the contracted balloon. After the balloon reaches an intended location in the body via a narrow living lumen, the balloon is then expanded to plastically deform and expand the stent, thereby distending the stenosed portion. The balloon is then contracted, though the stent stays expanded, thereby keeping the stenosed portion in a distended state.

For the reason mentioned above, the balloon on which a stent is mounted should be kept contracted and thin until the balloon reaches the intended location. Such method in which a balloon is folded to encircle an outer circumference of a shaft portion in the circumferential direction is known and an example is described in Japanese Patent Application Laid-Open No. 2008-86463.

However, when a balloon is folded to encircle the outer circumference of the shaft portion, portions of the balloon are stacked in layers, and the number of layers of each stack varies from portion to portion, which causes a variation in a thickness of the stacked of layers. Therefore, the outer diameter in a section perpendicular to the axis of the stent mounted on the balloon is rather large, which may make an insertion into a narrow living lumen difficult.

SUMMARY

In accordance with another aspect, a stent delivery system includes: a balloon which is expandable in an outer radial direction by injection of fluid into the balloon, wherein the balloon being is folded in a plurality of stacked layers around an outer circumference of an elongated shaft portion, and wherein the folded balloon possesses an outer circumference. The stent deliver system also includes a stent including a plurality of annular members, each annular member being comprised of a wire in an annular shape, with the plurality of annular parts being axially arranged, and with axially adjacent annular members connected to one another by at least one connecting part. All of the connecting parts are arranged on the outer circumference of the balloon in a manner that each of the connecting parts is positioned on a minimum-layered portion having a smallest number of stacked layers of the folded balloon.

The stent delivery system is configured so that the connecting parts of the stent are positioned on a minimum-layered portion of a balloon. Therefore, a region of the stent provided with the connecting part and relatively dense with elements of the stent is positioned on the minimum-layered portion of the folded balloon, and a portion of the folded balloon having many layers, that is, a portion having a great thickness, is positioned on a region relatively sparse in elements of the stent. Thereby, when the balloon is folded and the stent is mounted thereon, the outer diameter of the stent can be efficiently reduced.

The balloon can be folded around the outer circumference of the shaft portion, with the folded the balloon including an outer-folded portion in which a portion of the balloon is folded in a mountain fold toward the outer radial direction. When the connecting part is disposed on a portion other than the outer-folded portion, the outer-folded portion of the balloon, which tends to come off rather easily, is positioned at the region sparse in elements of the stent. Therefore, when the balloon is folded and the stent is mounted thereon, the outer diameter of the stent can efficiently be reduced.

The minimum-layered portion can be arranged to extend linearly along the direction of an axis of the shaft portion, and a plurality of the minimum-layered portions can be formed at an even interval in the circumferential direction, the material of the balloon is evenly distributed without creating dense or sparse portions, thereby, enabling efficient reduction of the diameter.

The connecting parts are preferably provided on a plurality of connecting part arranged regions which are evenly provided on the stent in the circumferential direction, and the number of the minimum-layered portions is an integer multiple of the number of the connecting part arranged regions. The plurality of connecting part arranged regions which are evenly distributed can thus be relatively easily positioned on the minimum-layered portion. Therefore, all the connecting parts can be rather easily arranged on the minimum-layered portion.

The number of the minimum-layered portions is preferably the same as the number of the connecting part arranged regions, and the connecting parts are arranged on all of the minimum-layered portions. All of the portions of the balloon having a relatively greater (greatest) thickness with many layers can be positioned on the region relatively sparse in elements of the stent. Thereby, the outer diameter of the stent mounted on the folded balloon can be efficiently reduced.

Each of the annular members has a plurality of turns along the direction of the stent axis, and a single line region is formed between the neighboring turns. When a single line region having a smallest density of elements constituting the stent is positioned on the outer-folded portion of the balloon, in which a portion of the balloon is folded in a mountain-fold toward the outer radial direction around the outer circumference of the shaft portion, the outer-folded portion of the balloon, which tends to come off rather easily, can be stored in a space between wires of the stent in the single line region having the smallest density. Thereby, the outer diameter of the stent mounted on the folded balloon can efficiently be reduced.

The folded balloon is preferably configured to include four minimum-layered portions, and so the outer diameter of the stent provided with four connecting part arranged regions can be efficiently reduced.

According to another aspect, a stent delivery system comprises: an outer tube possessing an inner surface; an inner tube positioned inside the outer tube and possessing an outer surface, with the inner surface of the outer tube being spaced from the outer surface of the inner tube so that a space exists between the inner surface of the outer tube and the outer surface of the inner tube; a balloon possessing a proximal portion fixed in a fluid-tight manner to the outer tube and also possessing a distal portion fixed in a fluid-tight manner to the inner tube; and a stent mounted on the folded balloon and encircling the outer circumference of the folded balloon. The space between the inner surface of the outer tube and the outer surface of the inner tube communicates with an interior of the balloon to allow expansion fluid to be introduced into the interior of the balloon to inflate the balloon and cause the balloon to expand in a radial outer direction. The balloon is folded around an outer circumference of the inner tube in a plurality of stacked layers so that the plurality of stacked layers overlie one another. The folded balloon includes a plurality of circumferentially spaced apart first layered portions and a plurality of circumferentially spaced apart second layered portions, with the first layered portions and the second layered portions circumferentially alternating with one another so that one of the first layered portions is positioned circumferentially between each successive pair of second layered portions, and with the first layered portion of the folded balloon possessing a total number of the stacked layers and the second layered portion of the folded balloon possessing a total number of the stacked layers. The total number of the stacked layers of the folded balloon in the first layered portions is different from the total number of stacked layers of the folded balloon in each of the second layered portions, and the total number of the stacked layers in the first layered portion is greater than the total number of the stacked layers in all other circumferential portions of the folded balloon. The stent includes a plurality of wavy-shaped annular members, with the wavy-shaped annular members being axially arranged, and with axially adjacent annular members connected to one another by at least one connecting part. All of the connecting parts of the stent are arranged on the outer circumference of the balloon such that each connecting part is circumferentially spaced from and does not overlie any of the first layered portions.

According to another aspect, a stent delivery system comprises: an outer tube possessing an inner surface; an inner tube positioned inside the outer tube and possessing an outer surface, with the inner surface of the outer tube being spaced from the outer surface of the inner tube so that a space exists between the inner surface of the outer tube and the outer surface of the inner tube; a balloon possessing a proximal portion fixed in a fluid-tight manner to the outer tube and also possessing a distal portion fixed in a fluid-tight manner to the inner tube; and a stent mounted on the folded balloon and encircling the outer circumference of the folded balloon. The space between the inner surface of the outer tube and the outer surface of the inner tube communicates with an interior of the balloon to allow expansion fluid to be introduced into the interior of the balloon to inflate the balloon and cause the balloon to expand in a radial outer direction. The balloon is folded around an outer circumference of the inner tube in a plurality of stacked layers so that the plurality of stacked layers overlie one another. The folded balloon includes a plurality of circumferentially spaced apart first layered portions and a plurality of circumferentially spaced apart second layered portions, with the first layered portions and the second layered portions circumferentially alternating with one another so that one of the first layered portions is positioned circumferentially between each successive pair of second layered portions. The first layered portion of the folded balloon possesses a total number of the stacked layers and the second layered portion of the folded balloon possesses a total number of the stacked layers, with the total number of the stacked layers of the folded balloon in the second layered portions being different from and less than the total number of stacked layers of the folded balloon in each of the first layered portions. The stent encircles the outer circumference of the folded balloon includes a plurality of wavy-shaped annular members that are axially arranged, with axially adjacent annular members connected to one another by at least one connecting part, and all of the connecting parts of the stent being arranged on the outer circumference of the balloon such that each connecting part is positioned at and extends along one of the second layered portions of the folded balloon.

DETAILED DESCRIPTION

Figure 1:
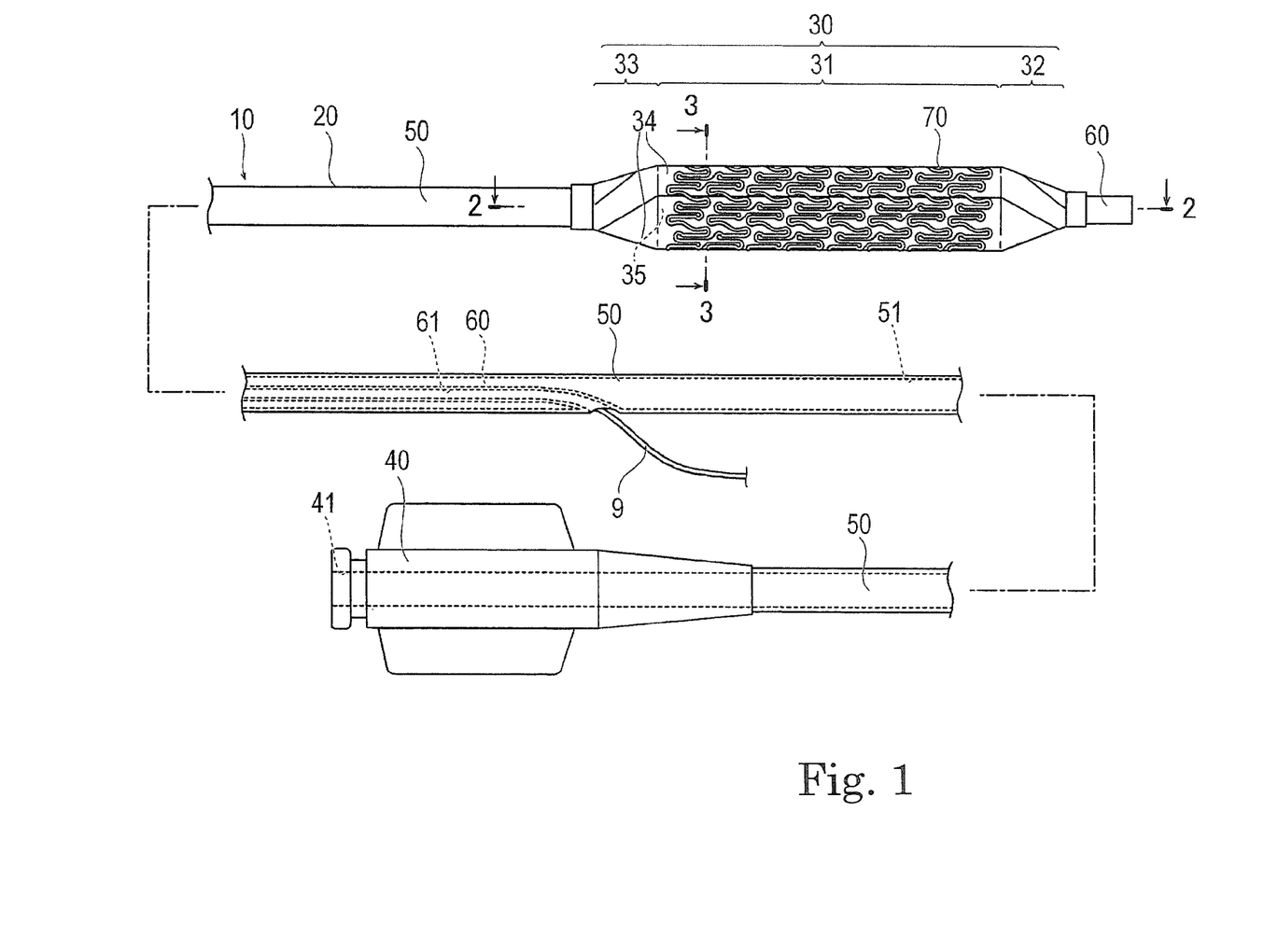
FIG. 1 is a plan view of a stent delivery system according to one embodiment disclosed here.

Referring initially to FIG. 1, set forth below is a description of an embodiment of the stent delivery system representing an example of the stent delivery system disclosed here. To facilitate an understanding of the disclosure here, ratios of dimensions in the drawings may be magnified and may be different from actual ratios.

A stent delivery system according to the present embodiment includes a balloon catheter 10 and a stent 70 as illustrated in FIG. 1. The balloon catheter 10 is used for indwelling the stent 70 in a stenosed portion in a living lumen such as a blood vessel, a bile duct, a trachea, an esophagus, a urethrfa, etc. In the specification, a portion of the stent delivery system which is inserted into a lumen is referred to as a "distal end" or a "distal end side", and a portion closer to an operator is referred to as a "proximal end" or a "proximal end side".

The balloon catheter 10 includes an elongated catheter main part 20, a balloon 30 which is provided on the distal end portion of the catheter main part 20 to support the stent, and a hub 40 which is fixed to the proximal end of the catheter main part 20.

The catheter main part 20 includes an outer tube 50 which is a cylindrical part having an opening at each of the distal end and proximal ends of the cylindrical tube, and an inner tube 60 (shaft portion) arranged inside the outer tube 50. An expansion lumen 51, in which expansion fluid for expanding the balloon 30 flows, is formed or located inside the outer tube 50. That is, the inner surface of the outer tube 50 is spaced from the outer surface of the inner tube 60 so that a space exists between the inner surface of the outer tube 50 and the outer surface of the inner tube 60 permitting an expansion fluid to be introduced into the interior of the balloon. The expansion fluid may be gas or liquid, for example, helium gas, $CO_2$ gas, or $O_2$ gas may be used as a gas, and a saline or a contrast medium may be used as a liquid. A guide wire lumen 61 in which a guide wire 9 is inserted is formed or located inside the inner tube 60.

Figure 2:
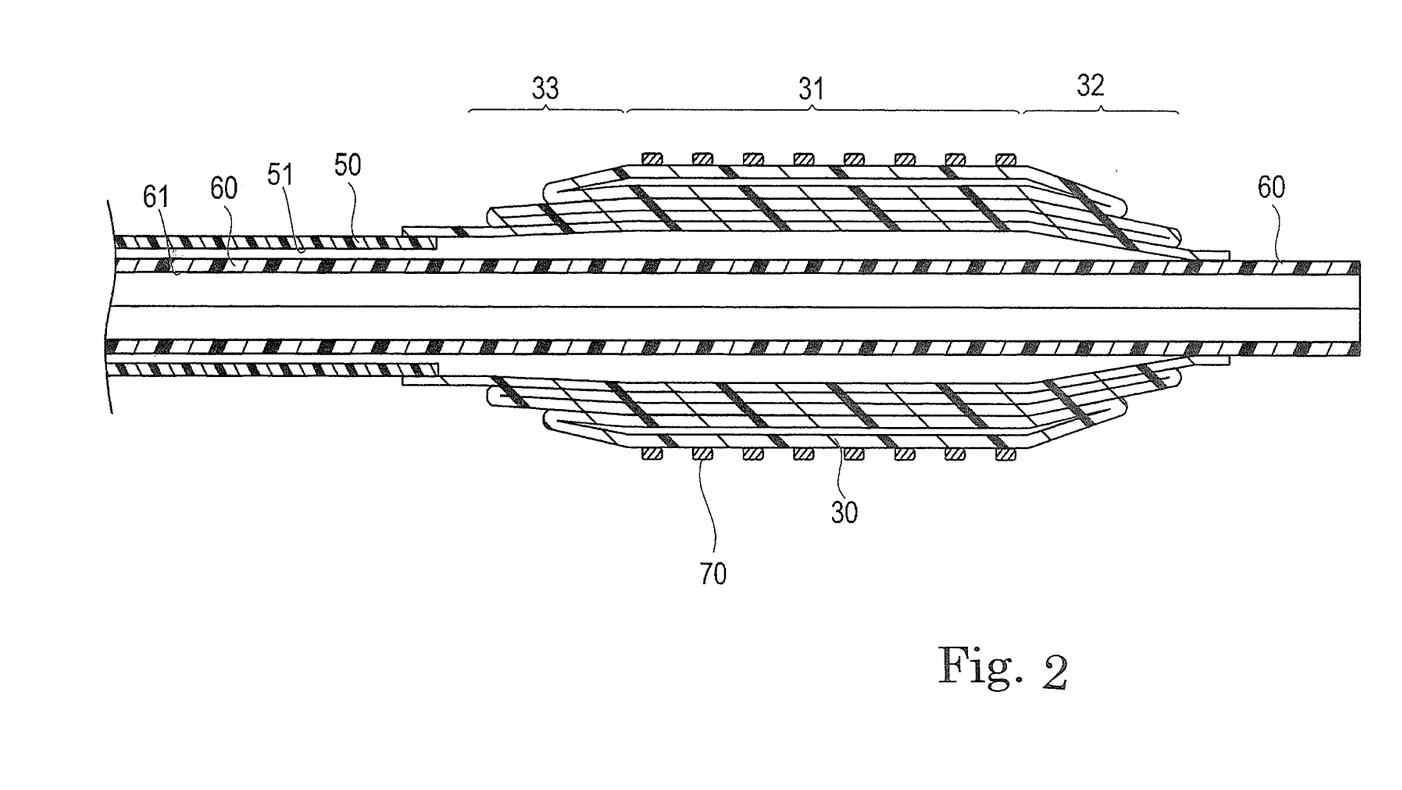
FIG. 2 is a longitudinal cross-sectional view of a distal end portion of the stent delivery system taken along the section line 2-2 in FIG. 1.

The inner tube 60 is configured as an elongated cylindrical tube. The distal end portion of the inner tube 60 penetrates through the inside of the balloon 30 and has an opening at the distal end of the inner tube which is located in the distal end side of the balloon 30 as illustrated in FIG. 2. That is, the open distal end of the inner tube 60 extends distally beyond the distal end of the balloon 30. A proximal end side of the inner tube 60 penetrates through a side wall of the outer tube 50 and is fluid-tightly fixed to the outer tube 50 using an adhesive or heat-sealing as illustrated in FIG. 1.

The hub 40 includes a proximal end opening part 41 which is connected to the expansion lumen 51 in the outer tube 50 to function as a port for injecting or draining the expansion fluid as illustrated in FIG. 1. The proximal end portion of the outer tube 50 is fluid-tightly fixed using an adhesive, heat-sealing, a fastener, or the like.

The outer tube 50 and the inner tube 60 are preferably formed of a material having a certain level of flexibility. Such material may be, for example, thermoplastic resin such as polyethylene, polypropylene, polybutene, ethylene-propylene copolymer, ethylene-vinyl acetate copolymer, ionomer, polyolefin such as a compound of two or more of the materials mentioned above, soft polyvinyl chloride resin, polyamide, polyamide elastomer, polyester, polyester elastomer, polyurethane, or fluoric resin, and may be silicone gum, latex rubber, or the like.

The material constituting the hub 40 may be, for example, thermoplastic resin such as polycarbonate, polyamide, polysulfone, polyarylate, or methacrylate-butylene-styrene copolymer.

Figure 4:
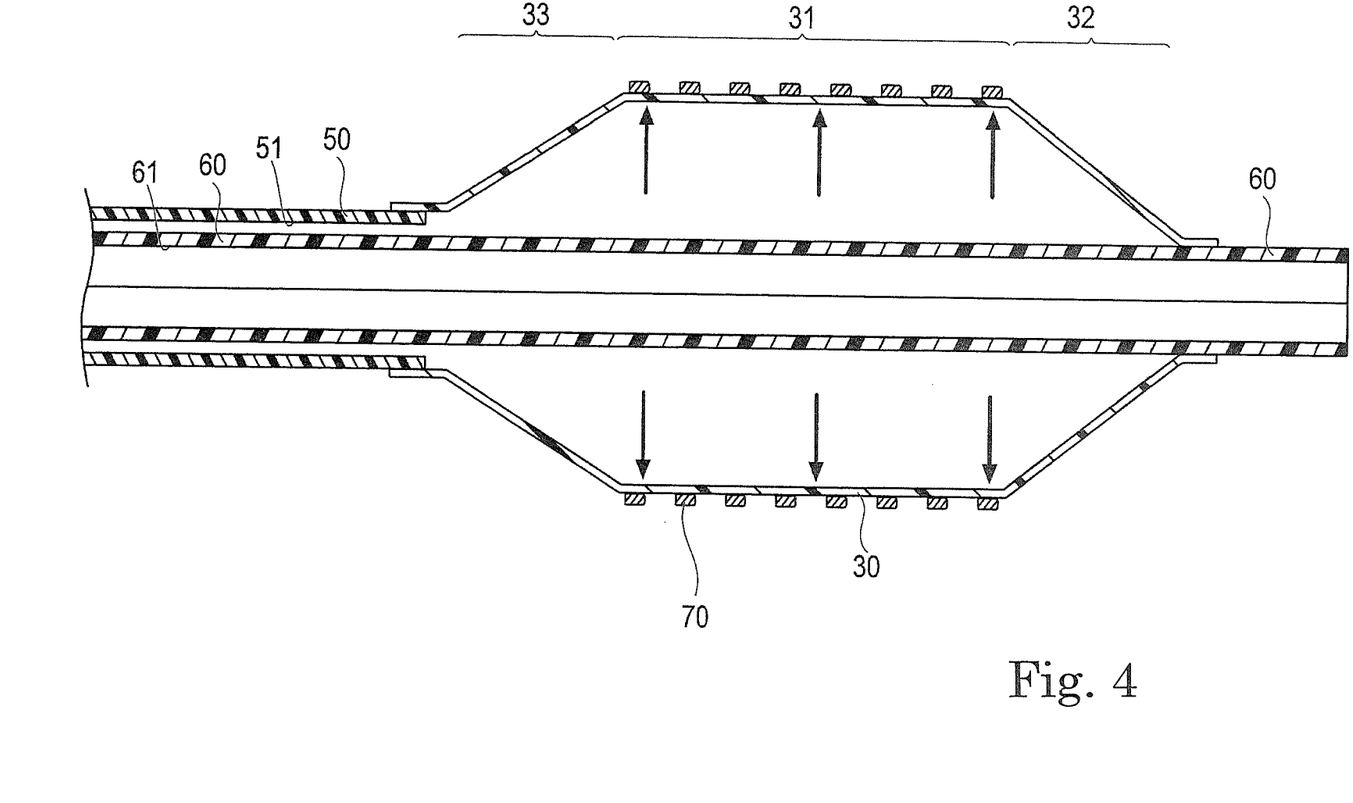
FIG. 4 is a longitudinal cross-sectional view illustrating an expanded balloon of a stent delivery system.

The balloon 30 expands the stent 70. That is, expanding the balloon 30 radially outwardly results in radial outward expansion of the stent 70. In order to efficiently expand the predetermined region of the stent, the balloon 30 includes a cylindrical portion 31 possessing a nearly cylindrical shape having an almost constant outer diameter, in a middle portion in the axial direction, as shown in FIG. 4, in which the balloon in expanded form is illustrated. A shape of the cross-section perpendicular to the axis of the cylindrical portion 31 need not be a circular. A first outer diameter reducing part 32, which tapers in outer diameter to possess a smaller outer diameter at the distal end, is provided in the distal end side of the cylindrical portion 31 of the balloon 30. A second outer diameter reducing part 33, which tapers in outer diameter to possess a smaller outer diameter at the proximal end, is provided in the proximal end side of the cylindrical portion 31 of the balloon 30.

The distal end side of the first diameter reducing part 32 is fluid-tightly fixed to the outer wall surface of the inner tube 60 using an adhesive, heat-sealing, or the like. The proximal end side of the second diameter reducing part 33 is fluid-tightly fixed to the outer wall surface of the distal end portion of the outer tube 50 using an adhesive, heat-sealing, or the like. Therefore, the inside of the balloon 30 is connected to the expansion lumen 51 formed in the outer tube 50, and the expansion fluid can be injected into the balloon via the expansion lumen 51 from the proximal end side. The balloon 30 expands by injecting the expansion fluid into the balloon, and is folded and contracted by draining the expansion fluid from the inside of the balloon.

Figure 3:
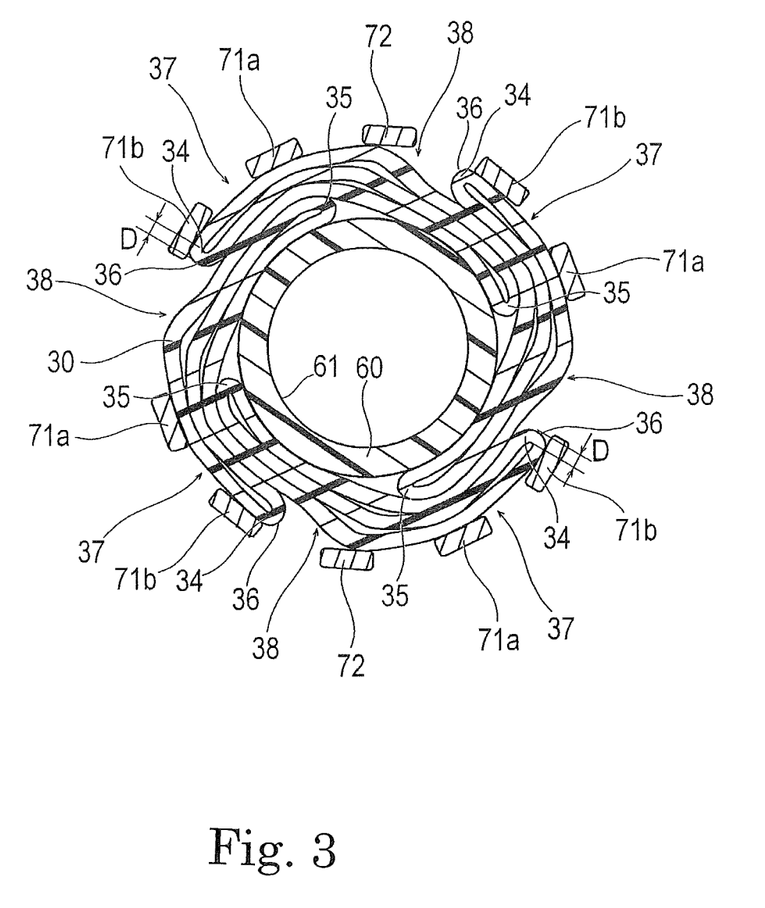
FIG. 3 is a cross sectional view of the stent delivery system taken along the section line 3-3 in FIG. 1.

The balloon 30 is shaped in a manner to be folded and encircle the outer circumference of the inner tube 60 in the circumferential direction when the balloon 30 is not expanded, as illustrated in FIGS. 1 to 3. Such balloon 30 can be formed by blow modeling, in which a tube, that is, a material, is heated in a die, pressurized from inside by a fluid to expand, and pressed against a die.

When the balloon 30 is folded to encircle the inner tube 60 as illustrated in FIG. 3, four outer-folded portions 34, each having a mountain fold toward the outer radial direction, and four inner-folded portions 35, each having a valley fold toward the outer radial direction, are formed. The outer-folded portions 34 are mountain-folded in that the outer-folded portions are positioned further radially outwardly relative to the inner-folded portions 35 on either circumferential side of the outwardly-folded portions. The inner-folded portions 35 are valley-folded in that the inner-folded portions are positioned further radially inwardly relative to the outer-folded portions 34 on either circumferential side of the inner-folded portions. The outer-folded portion 34 and the inner-folded portion 35 are arranged in a circumferential direction not to overlap with each other when the balloon is folded. That is, the outer-folded portions do not overlap with each other and do not overlap with the inner-folded portions, and the inner-folded portions 35 do not overlap with each other and do not overlap with the outer-folded portions 34. The outer-folded portions 34 are arranged at regular intervals of 90 degrees in the circumferential direction (i.e., circumferentially adjacent outer-folded portions are spaced apart by 90 degrees). Similarly, the inner-folded portions 35 are arranged at regular intervals of 90 degrees in the circumferential direction (i.e., circumferentially adjacent inner-folded portions are spaced apart by 90 degrees).

When the balloon 30 is folded to encircle the inner tube 60, the number of layers of material constituting the balloon 30, stacked around the outer circumference of the inner tube 60, varies in a circumferential direction among regions. In the embodiment, four maximum-layered portions 37 each of which has a stack of five layers of material of the balloon 30, and four minimum-layered portions 38 each having a stack of three layers of material of the balloon 30 are formed alternately in the circumferential direction. A portion in which the outer-folded portion 34 or the inner-folded portion 35 is provided sets a boundary between the maximum-layered portion 37 and the minimum-layered portion 38. Similar to the outer-folded portion 34 and the inner-folded portion 35, the maximum-layered portions 37 are arranged at a regular interval of 90 degrees in the circumferential direction (i.e., circumferentially adjacent maximum-layered portions 37 are spaced apart by 90 degrees). Similarly, minimum-layered portions 38 are arranged at an even interval of 90 degrees in the circumferential direction (i.e., circumferentially adjacent minimum-layered portions 37 are spaced apart by 90 degrees). The number of stacked layers varies according to the relative length of the balloon 30 in the circumferential direction against the outer circumference of the inner tube 60. The number of stacked layers may be smaller and the number of stacked layers may be larger. For example, the maximum-layered portion may be formed with three layers and the minimum-layered portion may be formed with one layer, or the maximum-layered portion may be formed with seven layers and the minimum-layered portion may be formed with five layers. Further, the maximum-layered portion and the minimum-layered portion may be formed with much larger number of layers. The outer-folded portion 34 is formed to have a width D corresponding to a film thickness of film-like material constituting the balloon 30, and a most distal end portion 36 which has a mountain fold, appears linearly on the outer surface of the balloon 30 encircling the inner tube 60.

The outer-folded portions 34 and the inner-folded portions 35 each extend linearly in the axial direction of the balloon 30 in the region corresponding to the cylindrical portion 31, that is, the middle portion in the axial direction of the balloon 30. Similarly, the maximum-layered portion 37 and the minimum-layered portion 38 also extend linearly in the axis direction of the balloon 30 in the region corresponding to the cylindrical portion 31, that is, the middle portion in the axial direction of the balloon 30.

The balloon 30 may be preferably formed of a material having a certain level of flexibility. Such material may be, for example, thermoplastic resin such as polyethylene, polypropylene, polybutene, ethylene-propylene copolymer, ethylene-vinyl acetate copolymer, ionomer, polyolefin such as a compound of two or more of the materials mentioned above, soft polyvinyl chloride resin, polyamide, polyamide elastomer, polyester, polyester elastomer, polyurethane, or fluoric resin, and may be silicone gum, latex rubber, or the like.

The stent 70 is a so-called balloon expandable stent which is mounted on the cylindrical portion 31 of the balloon 30 and expands (deforms plastically) by the outward expansion force of the balloon 30. The material constituting the stent 70 is preferably a metal having biocompatibility, for example, iron based alloy such as stainless steel, tantalum (tantalum alloy), platinum (platinum alloy), gold (gold alloy), cobalt based alloy such as cobalt-chromium alloy, titanium alloy, or niobium alloy.

Figure 5:
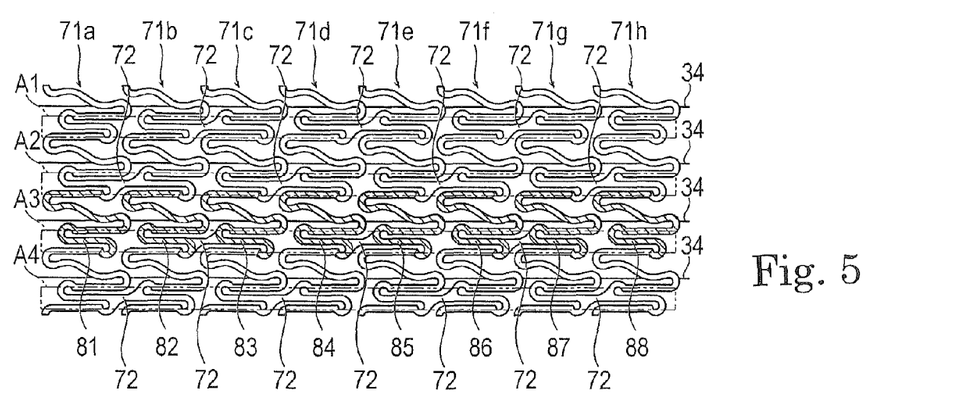
FIG. 5 is a development view of a stent to be positioned on a surface of a balloon of a stent delivery system.
Figure 6:
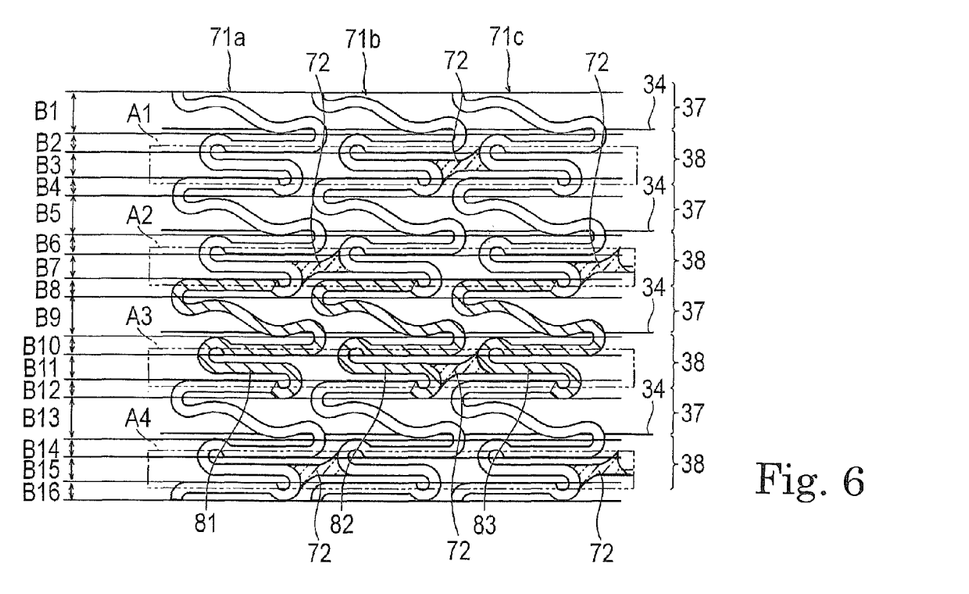
FIG. 6 is an enlarged development view of the stent shown in FIG. 5 in which a portion of FIG. 5 is enlarged.

The stent 70 is substantially formed in an cylindrical shape as illustrated in the development view in FIGS. 5 and 6 in which first to eighth ring-shaped or annular-shaped parts 71a, 71b, 71c, 71d, 71e, 71f, 71g and 71h are axially arranged, and axially adjacent pairs of the annular-shaped parts are connected by at least one connecting part. In the illustrated embodiment, axially adjacent pairs of the annular-shaped parts are connected by two connecting parts. That is, the annular-shaped part 71a and the second annular-shaped part 71b are connected by connecting parts 72, the second annular-shaped part 71b and the third annular-shaped part 71c are connected by connecting parts 72, the third annular-shaped part 71c and the fourth annular-shaped part 71d are connected by connecting parts 72, the fourth annular-shaped part 71d and the fifth annular-shaped part 71e are connected by connecting parts 72, the fifth annular-shaped part 71e and the sixth annular-shaped part 71f are connected by connecting parts 72, the sixth annular-shaped part 71f and the seventh annular-shaped part 71g are connected by connecting parts 72, and the seventh annular-shaped part 71g and the eighth annular-shaped part 71h are connected by connecting parts 72. Hereinafter, the first to eighth annular-shaped parts 71a, 71b, 71c, 71d, 71e, 71f, 71g and 71h will generally or generically referred to as an annular-shaped part or annular member 71. The number of annular members 71 is not limited to eight as long as the number is two or more.

The first annular-shaped part 71a is comprised of a plurality of curved-line patterns 81 (one such curved-line pattern 81 is cross-hatched in FIGS. 5 and 6) chained or connected together to form the annular shape, specifically a wavy-shaped annular member. Similarly, the second ring-shaped part 71b is comprised of a plurality of curved-line patterns 82 chained or connected together to form the annular shape (wavy-shaped annular member), the third ring-shaped part 71c is comprised of a plurality of curved-line patterns 83 chained or connected together to form the annular shape (wavy-shaped annular member), the fourth ring-shaped part 71d is comprised of a plurality of curved-line patterns 84 chained or connected together to form the annular shape (wavy-shaped annular member), the fifth ring-shaped part 71e is comprised of a plurality of curved-line patterns 85 chained or connected together to form the annular shape (wavy-shaped annular member), the sixth ring-shaped part 71f is comprised of a plurality of curved-line patterns 86 chained or connected together to form the annular shape (wavy-shaped annular member), the seventh ring-shaped part 71g is comprised of a plurality of curved-line patterns 87 chained or connected together to form the annular shape (wavy-shaped annular member), and the eighth ring-shaped part 71h is comprised of a plurality of curved-line patterns 88 chained or connected together to form the annular shape (wavy-shaped annular member).

Each of the curved-line patterns 81 to 88 is M-shaped and is formed from a metal wire having a substantially uniform width with turns. The metal wire is formed to have a rectangular section with a width of about, for example, 100 μm, and a thickness of about, for example, 1 to 100 μm. The width and thickness of the metal wire can suitably be varied and are not limited to the values described above.

The connecting part(s) 72 between the first annular-shaped part 71a and the second annular-shaped part 71b is a connecting part between the curved-line pattern 81 constituting a part of the first annular-shaped part 71a and the curved-line pattern 82 constituting a part of the second annular-shaped part 71b as illustrated as a region shown in dashed lines in FIG. 6. As illustrated in FIG. 6, the connecting parts 72 themselves do not include a curved-line pattern. Similarly, each of the connecting parts 72 between the second ring-shaped part 71b and the third ring-shaped part 71c, between the third ring-shaped part 71c and the fourth ring-shaped part 71d, between the fourth ring-shaped part 71d and the fifth ring-shaped part 71e, between the fifth ring-shaped part 71e and the sixth ring-shaped part 71f, between the sixth ring-shaped part 71f and the seventh ring-shaped part 71g, and between the seventh ring-shaped part 71g and the eighth ring-shaped part 71h, is defined as a portion between the two curved-line patterns at both sides or ends of the connecting part 72, and the connecting parts 72 themselves do not include a curved-line pattern.

All the connecting parts 72 existing in the stent 70 are arranged at an even interval in the circumferential direction of the stent 70. The circumferential spacing between all of the connecting parts 72 connecting two axially adjacent annular members 71 is the same; and the circumferential spacing between the connecting parts 72 connecting two axially adjacent annular members 71 is the same as the circumferential spacing between the connecting parts 72 connecting all other axially adjacent annular members 71. Each of the connecting parts 72 is positioned on either of four connecting part arranged regions A1 to A4 which extends parallel to the axis direction of the inner tube 60 (shaft portion). Therefore, all the connecting parts 72 are positioned on the minimum-layered portion 38 of the balloon 30, that is, the portion other than the outer-folded portion 34 of the balloon 30 which tends to come off easily. The total number of connecting part arranged regions A1 to A4 is the same as the total number of the minimum-layered portions 38 and is also the same as the total number of the outer-folded portions 34.

Each of the annular-shaped parts 71 is a wave-shaped member having a plurality of turns along the axis direction of the stent 70, and single line regions B1-B16 are formed between the circumferentially adjacent or neighboring turns as illustrated in FIG. 6. Among the single line regions B1-B16, the single line regions B1, B5, B9 and B13 do not include the connecting part 72 and therefore, a density of elements constituting the stent 70 in the single line regions B1, B5, B9 and B13 is smaller than those in other single line regions B2 to B4, B6 to B8, B10 to B12, and B14 to B16. The single line regions B1, B5, B9 and B13 having the smallest density of elements forming the stent are positioned on the outer-folded portion (mountain-fold) 34 of the balloon 30.

An example of an operation using a stent delivery system according to the above-described embodiment is now set forth, taking as an example a situation in which the stent delivery system is used for curing or treating a stenosed portion of a blood vessel.

Before curing or treating a stenosed portion of a blood vessel, the air in a balloon 30 and an expansion lumen 51 is purged as much as possible and substituted with expansion fluid. At this moment, the balloon 30 is folded and a stent 70 is mounted on the outer circumference of the balloon 30 (see FIGS. 1 to 3).

A sheath is indwelled in a blood vessel of a patient using, for example, the Seldinger Method, and a guide wire 9 and a balloon catheter 10 are inserted into the blood vessel from the inside of the sheath, while the guide wire 9 is inserted in the guide wire lumen 61 of the stent delivery system. Then, the balloon catheter 10 proceeds, guided by the guide wire 9, and the balloon 30 reaches the stenosed portion.

Figure 7:
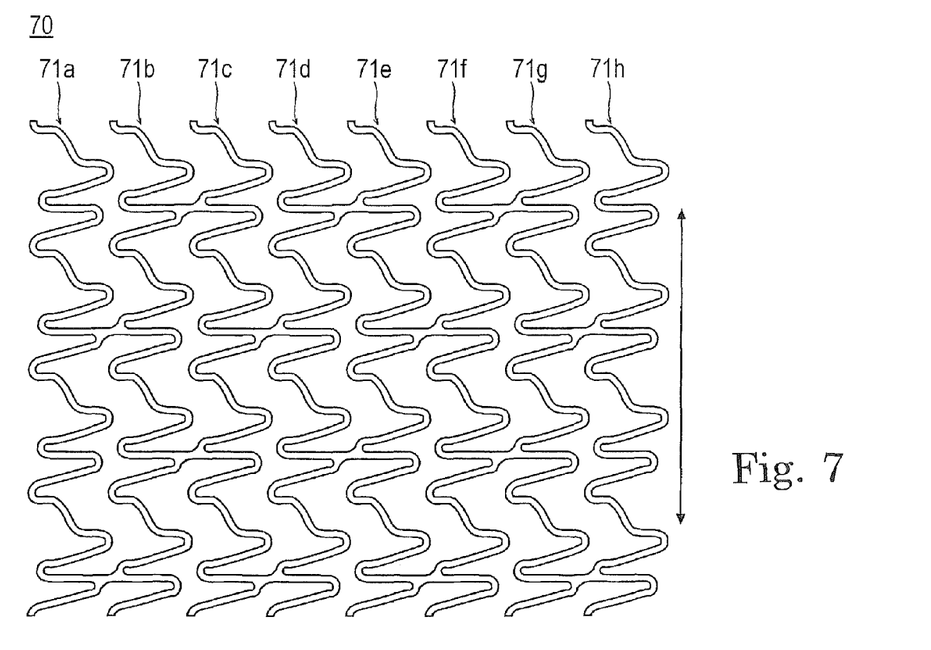
FIG. 7 is a development view illustrating a stent expanded by a balloon.

While the balloon 30 is positioned in the stenosed portion, a predetermined amount of expansion fluid is injected from a proximal end opening part 41 of the hub 40 using an indeflator, a syringe, a pump, or the like, so as to supply the expansion fluid into the interior of the balloon 30 via the expansion lumen 51 to expand the balloon 30 from the folded state, as illustrated in FIG. 4. Consequently, the cylindrical portion 31 of the balloon 30 plastically deforms and expands the stent 70 as illustrated in FIG. 7, thereby distending the stenosed portion by the stent 70.

The expansion fluid is then suctioned and drained from the proximal end opening part 41, thereby contracting the balloon 30 to the folded state. In this manner, the stent 70 is indwelled in the stenosed portion in an expanded state. The guide wire 9 and the balloon catheter 10 are then evulsed or removed from the blood vessel via the sheath to complete the operation.

In the stent delivery system according to this embodiment, because all of the connecting parts 72 of the stent 70 are positioned on a minimum-layered portion 38 of the balloon 30, the region of the stent in which each connecting part 72 is provided and therefore the region of the stent which is relatively dense with elements of the stent 70 is positioned on the minimum-layered portion 38 of the balloon having relatively lesser thickness, and the portion which is relatively sparse in elements of the stent 70 is positioned on a portion of the balloon having a greater thickness with many layers of the balloon 30 (maximum-layered portion 37). Consequently, material of the balloon 30 constituting the maximum-layered portion 37 having a relatively greater thickness, is stored or located in spaces between wires of the stent 70 in the portions that are relatively sparse in elements of the stent 70. Thereby, when the balloon 30 is folded and the stent is mounted on the folded balloon, the outer diameter of the stent can efficiently be reduced.

Since the balloon 30 includes an outer-folded portion 34 in which a portion of the balloon is folded in a mountain-fold toward the outer radial direction around the outer circumference of the inner tube 60, and the connecting part 72 is arranged on the portion of the balloon other than the outer-folded portion 34, the outer-folded portion 34 of the balloon 30, which tends to come off relatively easily, is positioned on the portion of the stent 70 that is relatively sparse in elements. Thereby, when the balloon 30 is folded and the stent is mounted on the balloon, the outer diameter of the stent can efficiently be reduced.

Because a plurality of the minimum-layered portions 38, each of which linearly extends along the axial direction of the inner tube 60 (i.e., parallel to the axis of the inner tube 60), is arranged at the same or a common circumferential intervals, the minimum-layered portions 38 are arranged at an even interval. Therefore, the material of the balloon 30 is evenly distributed without creating dense or sparse portions, thereby, enabling efficient reduction of the diameter.

Each of the connecting parts 72 is provided in one of a plurality of connecting part arranged regions A1 to A4 located at equal circumferential intervals of the stent 70, and so there are no connecting parts 72 provided at a portion of the circumference of the folded balloon other than the connecting part arranged regions A1 to A4. The total number of the minimum-layered portions 38 is an integral multiple (1 in this disclosed embodiment) of the total number of the connecting part arranged regions A1 to A4. Thus, the plurality of connecting part arranged regions A1 to A4 of the stent, which are arranged at equal intervals, can be rather easily matched to the location of the minimum-layered portions 38 of the balloon, which are also arranged at equal intervals. Consequently, all the connecting parts 72 provided in the connecting part arranged regions A1 to A4 can be relatively easily positioned on the minimum-layered portions 38.

Since the total number of the minimum-layered portions 38 is same as the total number of the connecting part arranged regions A1 to A4, the connecting parts 72 can be positioned on all of the minimum-layered portions 38, and thereby, the portion having a relatively greater thickness with many layers of the balloon 30 (maximum-layered portion 37) can be efficiently positioned in the regions relatively sparse in elements of the stent 70. Thereby, when the balloon 30 is folded and the stent 70 is mounted on the balloon, the outer diameter of the stent can be efficiently reduced.

Also, a plurality of turns along the axial direction of the stent 70 in each annular-shaped part 71 forms single line regions B1 to B16 in the stent 70. Since the single line regions B1, B5, B9, and B13 having the smallest density of elements constituting the stent 70 are positioned on the outer-folded portion 34 of the balloon 30, the outer-folded portion 34 of the balloon 30, which tends to come off relatively easily, can be stored in a space between the wires of the stent 70 in the single line regions B1, B5, B9, and B13 having the smallest density. Thereby, when the balloon 30 is folded and the stent 70 is mounted on the balloon, the outer diameter of the stent can efficiently be reduced.

Further, when four minimum-layered portions 38 are provided, the outer diameter of the stent 70 provided with four connecting part arranged regions A1 to A4 can be efficiently reduced.

The present invention is not limited to the embodiment described above, as variations can be made by those skilled in the art. For example, four connecting part arranged regions A1 to A4, four minimum-layered portions 38, and four outer-folded portions 34 are provided in this illustrated and described embodiment disclosed by way of example. However, these numbers are not limited and may be three or less, or five or more.

Figure 8:
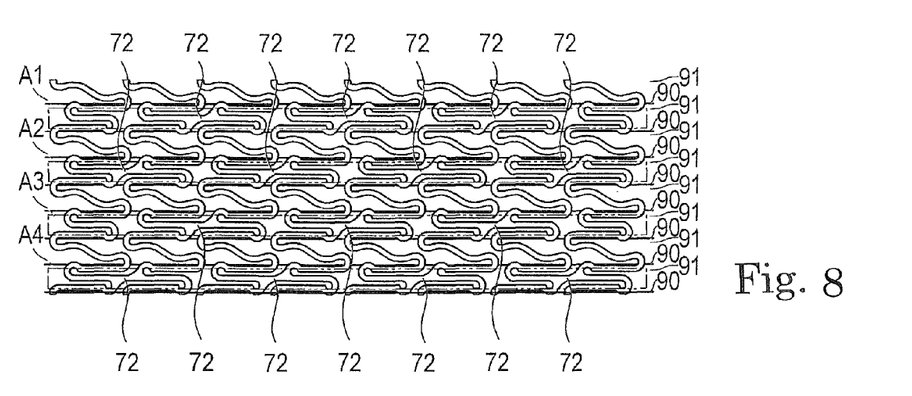
FIG. 8 is a development view of a stent positioned on the surface of a balloon illustrating a variation of the stent delivery system representing another example of the stent delivery system disclosed here.

Further, the total number of outer-folded portions and the total number of minimum-layered portions need not be same as the total number of the connecting part arranged regions A1 to A4. The total number of the outer-folded portions and the total number of the minimum-layered portions is preferably an integral multiple (e.g., 1, 2, 3, etc.) of the total number of the connecting part arranged regions. Referring to FIG. 8, the total number of the outer-folded portions 90 is eight, the total number of the minimum-layered portions 91 is also eight, and these numbers represent an integral multiple (two) of the total number of the connecting part arranged regions A1 to A4 which is four.

Figure 9:
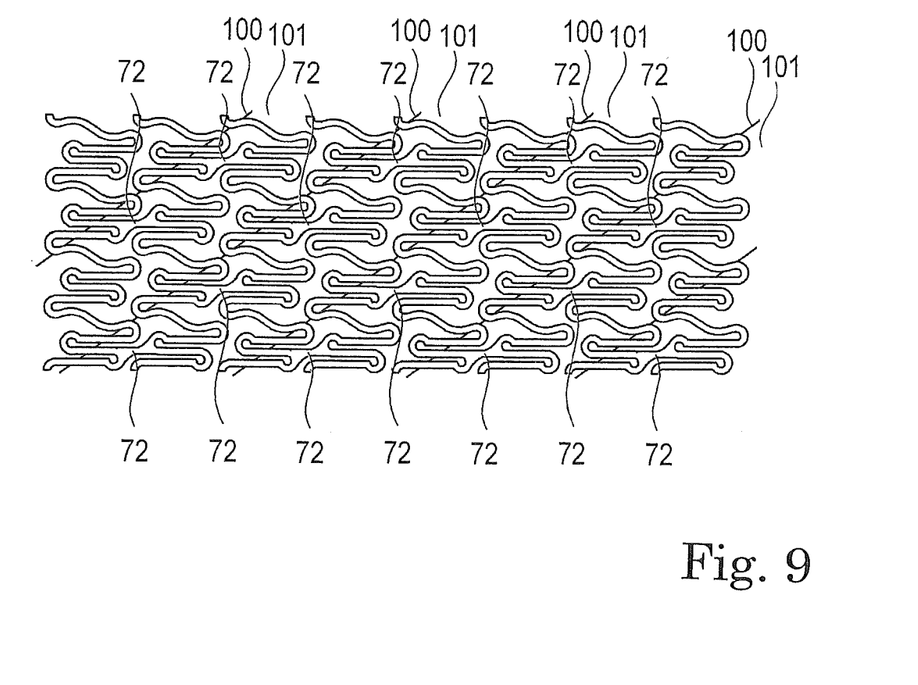
FIG. 9 is a development view of a stent positioned on a surface of a balloon illustrating another variation of the stent delivery system representing another example of the stent delivery system disclosed here.

Also, according to another variation illustrated in FIG. 9, an outer-folded portion 100 and a minimum-layered portion 101 need not be parallel to the axis of the inner tube 60. For example, the outer-folded portion 100 and the minimum-layered portion 101 may be inclined (obliquely inclined) relative to the axis of the inner tube 60. Further, the connecting part arranged regions A1 to A4 may be formed to be inclined (obliquely inclined) relative to the axis of the inner tube 60.

Further, the configuration of the stent is not limited as long as the connecting part is provided. Also, in the embodiment described above, each of the connecting parts 72 is defined as a portion which does not include curved-line patterns. However, the connecting part 72 need not be defined in this manner. That is, the stent may be configured such that the connecting parts 72 are not so clearly distinguished from the curved-line pattern so that there are no clear boundaries between the curved-line pattern and the connecting parts 72. For example, in a case in which the curved-line pattern cannot be defined precisely enough to define which region is included in the connecting part, a shape of the annular-shaped part which is connected to the connecting part may be defined as a portion having the same width as the metal wire in the vicinity of the connecting part. Thereby, the boundary between the ring-shaped part and the connecting part is defined and the region of the connecting part may clearly be defined.

The detailed description above describes an embodiment of a stent delivery system disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising: an outer tube possessing an inner surface; an inner tube positioned inside the outer tube and possessing an outer surface, the inner surface of the outer tube being spaced from the outer surface of the inner tube so that a space exists between the inner surface of the outer tube and the outer surface of the inner tube; a balloon possessing a proximal portion fixed in a fluid-tight manner to the outer tube and also possessing a distal portion fixed in a fluid-tight manner to the inner tube, the space between the inner surface of the outer tube and the outer surface of the inner tube communicating with an interior of the balloon to allow expansion fluid to be introduced into the interior of the balloon to inflate the balloon and cause the balloon to expand in a radial outer direction; the balloon configured to be in a folded configuration around an outer circumference of the inner tube in a plurality of stacked layers so that the plurality of stacked layers overlie one another prior to introduction of any fluid into the balloon, the folded balloon including a plurality of circumferentially spaced apart first layered portions and a plurality of circumferentially spaced apart second layered portions, the first layered portions and the second layered portions circumferentially alternating with one another so that one of the first layered portions is positioned circumferentially between each successive pair of second layered portions, the first layered portions of the folded balloon possessing a total number of the stacked layers and thereby define a plurality of maximum-layered portions, and the second layered portions being different from and less than the total number of stacked layers of the folded balloon and thereby define a plurality of minimum-layered portions; and a stent mounted on the balloon in the folded configuration and encircling the outer circumference of the folded balloon, the stent including a plurality of wavy-shaped annular members, the wavy-shaped annular members being axially arranged, with axially adjacent annular members connected to one another by at least one connecting part, all of the connecting parts of the stent being arranged on the outer circumference of the balloon such that each connecting part is positioned at and extends along one of the minimum-layered portions of the folded balloon such that an outer diameter of the stent is minimized.

2. The stent delivery system according to claim 1, wherein each of the second layered portions extends linearly along an axial direction of the inner tube.

3. The stent delivery system according to claim 1, wherein the second layered portions are arranged at equal intervals in a circumferential direction of the balloon.

4. The stent delivery system according to claim 1, wherein the first layered portions are arranged at equal intervals in a circumferential direction of the balloon, and wherein the second layered portions are arranged at equal intervals in the circumferential direction of the balloon.

5. The stent delivery system according to claim 1, wherein the connecting parts are provided at respective connecting part arranged regions on the stent at equal intervals in the circumferential direction so that all of the connecting parts are in one of the connecting part arranged regions, the balloon including a total number of the second layered portions, the stent including a total number of the connecting part arranged regions, the total number of the second layered portions is an integral multiple of the total number of the connecting part arranged regions.

6. The stent delivery system according to claim 5, wherein the total number of the second-layered portions is same as the total number of the connecting part arranged regions.

7. A stent delivery system comprising: an outer tube possessing an inner surface; an inner tube positioned inside the outer tube and possessing an outer surface, the inner surface of the outer tube being spaced from the outer surface of the inner tube so that a space exists between the inner surface of the outer tube and the outer surface of the inner tube; a balloon possessing a proximal portion fixed in a fluid-tight manner to the outer tube and also possessing a distal portion fixed in a fluid-tight manner to the inner tube, the space between the inner surface of the outer tube and the outer surface of the inner tube communicating with an interior of the balloon to allow expansion fluid to be introduced into the interior of the balloon to inflate the balloon and cause the balloon to expand in a radial outer direction; the balloon configured to be in a folded configuration around an outer circumference of the inner tube in a plurality of stacked layers so that the plurality of stacked layers overlie one another prior to introduction of any fluid into the balloon, the folded balloon including a plurality of circumferentially spaced apart first layered portions and a plurality of circumferentially spaced apart second layered portions, the first layered portions and the second layered portions circumferentially alternating with one another so that one of the first layered portions is positioned circumferentially between each successive pair of second layered portions, the first layered portions of the folded balloon possessing a total number of the stacked layers and thereby define a plurality of maximum-layered portions, the total number of the stacked layers of the folded balloon in the first layered portions being different from a number of stacked layers of the folded balloon in each of the second layered portions, the total number of the stacked layers in the first layered portions being greater than a number of the stacked layers in all other circumferential portions of the folded balloon; and a stent mounted on the balloon in the folded configuration and encircling the outer circumference of the folded balloon, the stent including a plurality of wavy-shaped annular members, the wavy-shaped annular members being axially arranged, with axially adjacent annular members connected to one another by at least one connecting part, all of the connecting parts of the stent being arranged on the outer circumference of the balloon such that each connecting part is circumferentially spaced from and does not overlie any of the maximum-layered portions of the balloon such that an outer diameter of the stent is configured to be minimized.

8. The stent delivery system according to claim 7, wherein axially adjacent pairs of the wavy shaped annular members are connected by a total of two connecting parts.

9. The stent delivery system according to claim 7, wherein a minimum-layered portion is defined as the second layered portions in which the number of the stacked layers of the folded balloon is less than the total number of the stacked layers of the folded balloon in all other circumferential portions of the folded balloon.

10. The stent delivery system according to claim 7, wherein the first layered portions are arranged at equal intervals in a circumferential direction of the balloon, and wherein the second layered portions are arranged at equal intervals in the circumferential direction of the balloon.

11. The stent delivery system according to claim 7, wherein the connecting parts are provided at respective connecting part arranged regions on the stent at equal intervals in the circumferential direction so that all of the connecting parts are in one of the connecting part arranged regions, the balloon including a total number of the second layered portions, the stent including a total number of the connecting part arranged regions, the total number of the second layered portions is an integral multiple of the total number of the connecting part arranged regions.

12. A stent delivery system comprising: a balloon which is expandable in an outer radial direction by injection of fluid into the balloon, the balloon configured to be folded in a plurality of stacked layers around an outer circumference of an elongated shaft portion to thereby define a folded configuration prior to introduction of any fluid into the balloon, the folded configuration of the balloon possessing an outer circumference, the folded balloon including a plurality of circumferentially spaced apart first layered portions and a plurality of circumferentially spaced apart second layered portions, the first layered portions and the second layered portions circumferentially alternating with one another so that one of the first layered portions is positioned circumferentially between each successive pair of second layered portions, the first layered portions of the folded balloon possessing a total number of the stacked layers and thereby define a plurality of maximum-layered portions, and the second layered portions being different from and less than the total number of stacked layers of the folded balloon and thereby define a plurality of minimum-layered portions; and a stent including a plurality of annular members, each annular member being comprised of a wire in an annular shape, the plurality of annular members being axially arranged, with axially adjacent annular members connected to one another by at least one connecting part, all of the connecting parts being arranged on the outer circumference of the balloon in the folded configuration in a manner that each of the connecting parts is positioned on one of the plurality of a minimum-layered portions having a smallest number of stacked layers of the folded balloon such that, when the balloon is folded into the folded configuration and the stent is mounted on the balloon, an outer diameter of the stent can be minimized.

13. The stent delivery system according to claim 12, wherein the folded balloon includes an outer-folded portion in which a portion of the balloon is folded in a mountain-fold toward the outer radial direction around the outer circumference of the shaft portion, and each of the connecting parts are arranged on a portion of the outer circumference of the balloon other than the outer-folded portion.

14. The stent delivery system according to claim 12, wherein a plurality of the minimum-layered portions, each of which extends linearly along an axial direction of the shaft portion, is formed and arranged at equal intervals in a circumferential direction of the balloon.

15. The stent delivery system according to claim 14, wherein the connecting parts are provided at respective connecting part arranged regions on the stent at equal intervals in the circumferential direction, the balloon including a total number of the minimum-layered portions, the stent including a total number of the connecting part arranged regions, the total number of the minimum-layered portions is an integral multiple of the total number of the connecting part arranged regions.

16. The stent delivery system according to claim 15, wherein the total number of the minimum-layered portions is same as the total number of the connecting part arranged regions.

17. The stent delivery system according to claim 12, wherein each of the annular members includes a plurality of turns forming a wavy-shape, with an axial single line region between circumferentially adjacent turns, one of the single line regions having a smallest density of elements constituting the stent is positioned on an outer-folded portion of the folded balloon in which a portion of the balloon is folded in a mountain-fold that extends radially outwardly further than portions of the folded balloon on immediately adjacent circumferential sides of the mountain-fold.

18. The stent delivery system according to claim 12, wherein the folded balloon includes a plurality of the minimum-layered portions totaling four.

\* \* \* \* \*